US007002142B2

(12) United States Patent
Mullins et al.

(10) Patent No.: US 7,002,142 B2
(45) Date of Patent: Feb. 21, 2006

(54) DETERMINING DEW PRECIPITATION AND ONSET PRESSURE IN OILFIELD RETROGRADE CONDENSATE

(75) Inventors: Oliver C. Mullins, Ridgefield, CT (US); Go Fujisawa, Danbury, CT (US); Chengli Dong, Sugar Land, TX (US); Andrew Kurkjian, Sugar Land, TX (US); John Nighswander, Aberdeenshire (GB); Toru Terabayashi, Sagamihara (JP); Satoko Yoshida, Machida (JP); Hideki Kinjo, Sagamihara (JP); Henning Groenzin, Lexington, MA (US)

(73) Assignee: Schlumberger Technology Corporation, Ridgefield, CT (US)

( * ) Notice: Subject to any disclaimer, the term of this patent is extended or adjusted under 35 U.S.C. 154(b) by 191 days.

(21) Appl. No.: 10/309,850

(22) Filed: Dec. 3, 2002

(65) Prior Publication Data

US 2004/0000636 A1    Jan. 1, 2004

Related U.S. Application Data

(60) Provisional application No. 60/391,570, filed on Jun. 26, 2002.

(51) Int. Cl.
*G01V 8/00* (2006.01)
(52) U.S. Cl. .................................. 250/269.1; 356/128
(58) Field of Classification Search ............. 250/269.1; 356/128
See application file for complete search history.

(56) References Cited

U.S. PATENT DOCUMENTS 3,780,575 A    12/1973   Urbanosky ................... 73/152
3,859,851 A     1/1975   Urbanosky ................... 73/155

(Continued)

FOREIGN PATENT DOCUMENTS

EP         0 461 321 A1    12/1991

(Continued)

OTHER PUBLICATIONS

Downare, T.D. et al. "Visible and Near-Infrared Fluorescence of Crude Oils". *Applied Spectroscopy*, vol. 49, No. 6, (1995), pp. 754-764.

(Continued)

*Primary Examiner*—David Porta
*Assistant Examiner*—Shun Lee
(74) *Attorney, Agent, or Firm*—Jody Lynn DeStefanis; John L. Lee; Dale Gaudier

(57) ABSTRACT

A method and apparatus detects dew precipitation and determines dew precipitation onset pressure in a sample of formation fluid located downhole in an oilfield reservoir. In a preferred embodiment, the method includes (a) isolating a sample of formation fluid downhole; (b) illuminating the sample downhole with fluorescence excitation light; (c) measuring at least one characteristic of fluorescence short from the sample; (d) reducing pressure on the sample; (e) repeating steps (b) to (d); (f) detecting dew precipitation when a change is detected in a parameter that is a function of the at least one characteristic of fluorescence emission; and (g) setting dew precipitation onset pressure equal to pressure on the sample when the change in the parameter is detected. The parameter preferably is a function of fluorescence intensity and fluorescence red shift, and the change is an increase in fluorescence intensity and detection of fluorescence red shift. Also, the function includes a ratio of a measured intensity at a first wavelength to a reference intensity, and the reference intensity is a function of a measured intensity at a second wavelength.

15 Claims, 10 Drawing Sheets

U.S. PATENT DOCUMENTS

| | | | |
|---|---|---|---|
| 4,860,581 A | 8/1989 | Zimmerman et al. | 73/155 |
| 4,959,549 A * | 9/1990 | Haub et al. | 250/461.1 |
| 4,994,671 A | 2/1991 | Safinya et al. | 250/255 |
| 5,167,149 A | 12/1992 | Mullins et al. | 73/155 |
| 5,691,809 A | 11/1997 | Tackett et al. | 356/72 |
| 5,939,717 A | 8/1999 | Mullins | 250/255 |
| 6,016,191 A * | 1/2000 | Ramos et al. | 356/70 |
| 6,476,384 B1 | 11/2002 | Mullins et al. | |
| 2003/0193662 A1 * | 10/2003 | DiFoggio et al. | 356/128 |

FOREIGN PATENT DOCUMENTS

| | | |
|---|---|---|
| EP | 1 203 942 A1 | 5/2002 |
| WO | WO 01/20322 A1 | 3/2001 |

OTHER PUBLICATIONS

Mullins, O. C. et al. "Downhole Determination of GOR on Single-Phase Fluids by Optical Spectroscopy". *SPWLA 42nd Annual Symposium*, Paper M, (2001), pp. 1-14.

Ralston, C. Y. et al. "Quantum Yields of Crude Oils". *Applied Spectroscopy*, vol. 50, No. 12, (1996), pp. 1563-1568.

Wang, X. et al. "Fluorescence Lifetime Studies of Crude Oils", *Applied Spectroscopy*, vol. 48, No. 8, (1994), pp. 977-984.

\* cited by examiner

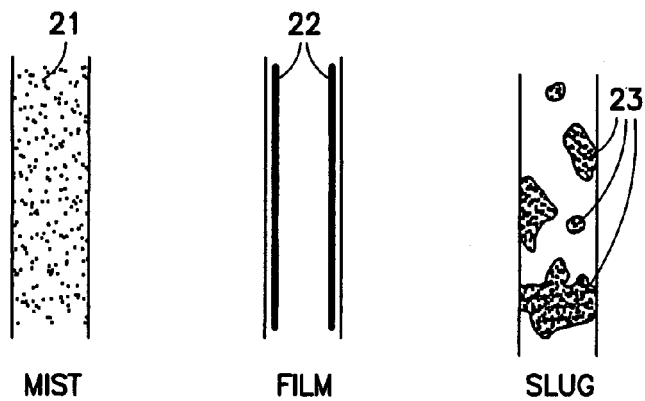
MIST
FIG.9A
FILM
FIG.9B
SLUG
FIG.9C
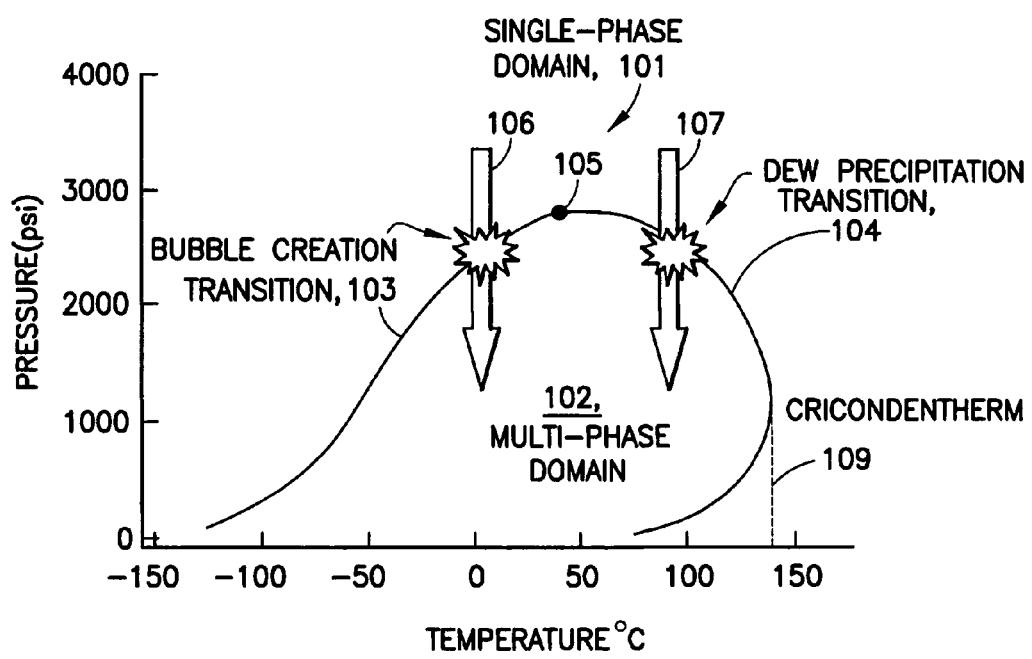
FIG.10
PRIOR ART

DETERMINING DEW PRECIPITATION AND ONSET PRESSURE IN OILFIELD RETROGRADE CONDENSATE

This application claims priority to co-owned, U.S. provisional application no. 60/391,570, filed Jun. 26, 2002, now expired.

FIELD OF THE INVENTION

The present invention is directed to evaluating new petroleum discoveries by analysis of fluid samples acquired by wireline fluid sampling (WFS) from an oilfield reservoir, and in particular to detecting and assessing dew precipitation in retrograde condensate fluid samples from deep hot oil and gas reservoirs.

BACKGROUND OF THE INVENTION

To evaluate a new petroleum discovery, it is necessary to acquire formation fluid samples for analysis. Often, the only economically viable way to acquire such samples is by open-hole wireline fluid sampling (WFS). However, WFS suffers two sources of error: (1) mud filtrate contamination, and (2) phase separation of formation fluid. The presence of either mud filtrate contamination or phase separation invalidates any ensuing analysis. Some prior art WFS tools provide real-time downhole detection of mud filtrate contamination or phase separation of formation fluid. When mud filtrate contamination or phase separation of formation fluid is detected in a sample, the sample is deemed invalid and is not analyzed.

The Schlumberger Optical Fluid Analyzer (OFA*) and the Schlumberger Live Fluid Analyzer (LFA*) are prior art WFS tools capable of real-time downhole detection of mud filtrate contamination. The OFA* detects water based mud contamination using near-infrared (NIR) spectrum analysis. The LFA* detects oil base mud (OBM) filtrate contamination using gas-oil ratio (GOR) analysis. (OBM has virtually zero GOR). The OFA* and the LFA* also detect one form of phase separation, bubble creation. The LFA* also detects gas phase using three methods. ("*" indicates Mark of Schlumberger). The three methods are: gas-phase detection by change in refractive index, gas-phase detection by temporal variation of methane peak, and gas-phase detection by lack of optical absorption. Neither of these analyzers, nor any other analyzer known to the inventors, provides a method for real-time downhole detection of another form of phase separation, dew precipitation.

The conditions which lead to bubble creation and dew precipitation in formation fluid are illustrated in a pressure/temperature diagram, generally known as a "Phase Diagram". FIG. 10 (prior art) is a phase diagram showing the conditions under which single phase flow in condensates (3300<GOR<50,000) changes to multi-phase flow under conditions of pressure reduction. It shows bubble creation and dew precipitation. The phase diagram of FIG. 10 shows that when the temperature is below the critical point, and the pressure is reduced, the pressure drop line will intersect the bubble line and some condensates will phase separate as discrete gas bubbles in a continuous liquid phase. The phase diagram also shows that when the temperature is between the critical point and the cricondentherm, and the pressure is reduced, the pressure drop line will intersect the dew precipitation line and some condensates will phase separate as dew (a discrete liquid phase in a continuous liquid phase).

It is also useful to note that petroleum fluids found in subsurface formations can be categorized by their gas/oil ratio (GOR). GOR is expressed in units of standard cubic feet of gas per stock tank barrel of oil, both at 1 atmosphere and 60° F. The categories are: black oils, GOR<2000; volatile oils, 2000<GOR<3300; condensates, 3300<GOR<50,000; wet gas, 50,000<GOR (but finite); dry gas, infinite GOR. The need for detection of dew precipitation in formation fluid exists for a range of petroleum fluid types including volatile oils, condensates, and wet gas.

Wireline fluid sampling (WFS) requires single-phase sampling because if phase separation occurs, then the differential mobility of the phases and the spatial separation of the phases virtually guarantee that the collected sample will not be representative of the formation fluid. Moreover, the process of wireline fluid sampling requires a pressure reduction below formation pressure to move the fluids, and this pressure reduction can cause phase separation. The most common phase separation encountered in WFS is the appearance of a gas phase and a liquid phase. Another common phase separation that can occur with a pressure reduction is asphaltene deposition. For wireline sampling of borehole fluids, it is necessary to recognize two-phase flow when it occurs in order to change flowline conditions to achieve single-phase flow and obtain a representative sample. Generally, pressure is the only adjustable parameter, so the flow type is monitored as a function of pressure. Higher pressure draw-downs are preferred in order to obtain pure formation samples in shorter time by reducing OBM filtrate fractions. However, larger pressure draw-downs are more likely to generate phase separation.

Retrograde condensates are condensates from formations where the temperature is between the fluid critical point (the pressure/temperature point at which distinctions between gaseous phase and liquid phase cease to exist) and the cricondentherm (the highest temperature in which dew is still able to precipitate out of the mixture). Refer to FIG. 10.

For the reasons given above, open-hole wireline sampling of retrograde condensates is unreliable for lack of method and apparatus for timely detection of dew precipitation. Therefore, there exists a need for method and apparatus for downhole detection of dew precipitation.

In a first embodiment illustrated in FIG. 6, the invention uses a measurement of fluorescence intensity, defined by steps 201–210. In a second (preferred) embodiment illustrated in FIG. 7, the invention uses a measurement of fluorescence intensity and a measurement of fluorescence red-shift, defined by steps 301–311. Preferably, the preferred embodiment also uses a measurement of optical absorption. In a third embodiment illustrated in FIG. 8, the invention uses a measurement of fluorescence lifetime, defined by steps 401–410.

Two prior art commercially available tools that allow several samples to be taken from the formation in a single logging run are the Schlumberger Modular Formation Dynamics Tester (MDT*) and the Schlumberger Repeat Formation Tester (RFT*). The MDT* tool includes a fluid analysis module to allow analysis of the fluids sampled by the tool. ("*" indicates Mark of Schlumberger). FIG. 1 of U.S. Pat. No. 3,859,851 shows a schematic diagram of a tool for testing earth formations and analysing the composition of fluids from the formation. The tool of U.S. Pat. No. 3,859,851 is suspended in borehole from the lower end of a logging cable that is connected in a conventional fashion to a surface system incorporating appropriate electronics and processing systems for control of the tool. The tool includes an elongated body that carries a selectively extendible fluid admitting assembly. Such fluid admitting assemblies are shown in U.S. Pat. Nos. 3,780,575; 3,859,851 and 4,860,581. The elongated body also carries selectively extendible anchoring members that are arranged on opposite sides of the body. The fluid admitting assembly is equipped for selectively sealing off or isolating portions of the wall of the borehole such that pressure or fluid communication with the adjacent earth formation is established. A fluid analysis module is also included within the tool body, through which the obtained fluid flows. The fluid can then be expelled through a port back into the borehole, or can be sent to one or more sample chambers for recovery at the surface.

The Schlumberger Modular Formation Dynamics Tester (MDT*) includes a Live Fluids Analyzer (LFA*) that determines the identity of the fluids in the MDT* flow stream and quantifies the oil and water content. In particular, U.S. Pat. No. 4,994,671 (hereby incorporated herein by reference) describes a borehole apparatus which includes a testing chamber, means for directing a sample of fluid into the chamber, a light source preferably emitting near infrared rays and visible light, a spectral detector, data base means, and processing means. Fluids drawn from the formation into the testing chamber are analysed by directing the light at the fluids, detecting the spectrum of the transmitted and/or backscattered light, and processing the information accordingly (preferably based on information in the data base relating to different spectra), in order to quantify the amount of water and oil in the fluid.

SUMMARY OF THE INVENTION

The invention provides a method for detecting dew precipitation in a sample of formation fluid located downhole in an oilfield reservoir. In a preferred embodiment, the method includes (a) isolating a sample of formation fluid downhole; (b) illuminating the sample downhole with fluorescence excitation light; (c) measuring at least one characteristic of fluorescence emission from the sample; (d) reducing pressure on the sample; (e) repeating steps (b) to (d); (f) detecting dew precipitation when a change is detected in a parameter that is a function of the at least one characteristic of fluorescence emission; and (g) setting dew precipitation onset pressure equal to pressure on the sample when the change in the parameter is detected. In this preferred embodiment, the parameter is a function of fluorescence intensity and fluorescence red shift, and the change is an increase in fluorescence intensity and detection of fluorescence red shift. Also, the function includes a ratio of a measured intensity at a first wavelength to a reference intensity. Also, the reference intensity is a function of a measured intensity at a second wavelength.

Preferably, isolating a fluid sample downhole includes enclosing the sample in a fluid sample cell having a window; illuminating the fluid sample includes selectively illuminating the fluid sample in an interrogation volume adjacent to the window; and measuring at least one characteristic of fluorescence emission includes measuring fluorescence intensity emitted from the interrogation volume.

In an alternative embodiment, the parameter is a function of fluorescence lifetime, and the change is decrease in fluorescence lifetime.

In another alternative embodiment, the fluorescence excitation light is polarized and directed onto the window at the Brewster angle. Also, the fluorescence excitation light is polarized in a first direction, and fluorescence light received by a detector is polarized in a second direction, the second direction being orthogonal to the first direction.

In another embodiment the invention provides a method including (a) illuminating the fluid sample downhole with fluorescence excitation light at a first excitation wavelength; (b) measuring fluorescence intensity emitted from the fluid sample under reduced pressure in a fluid sample cell to produce a measured intensity value; and (c) detecting dew precipitation when the measured intensity value is greater than a reference intensity value.

The invention also provides tool for detecting dew precipitation in a fluid sample located downhole in an oilfield reservoir. In a preferred embodiment, the tool includes a tool body with a fluid sample cell adapted to take a sample of formation fluid downhole in the oilfield reservoir; means for isolating a sample of formation fluid downhole; means for illuminating the sample downhole with fluorescence excitation light; means for repeatedly reducing pressure on the sample and measuring at least one characteristic of fluorescence emmission from the sample; and means for detecting dew precipitation when a change is detected in a parameter that is a function of the at least one characteristic of fluorescence emission.

In another embodiment, the tool includes a tool body with a fluid sample cell adapted to take a sample of formation fluid downhole in the oilfield reservoir; means for illuminating the fluid sample downhole with fluorescence excitation light at a first excitation wavelength; means for measuring fluorescence intensity emitted from the fluid sample under reduced pressure in a fluid sample cell to produce a measured intensity value; and means for detecting dew precipitation when the measured intensity value is greater than a reference intensity value.

BRIEF DESCRIPTION OF THE DRAWINGS

FIGS. 9A, 9B, and 9C illustrate three forms of dew, mist, film, and slug flow, respectively.

FIG. 10 is a phase diagram (prior art) showing phase separations in formation fluid.

DETAILED DESCRIPTION

Figure 1:
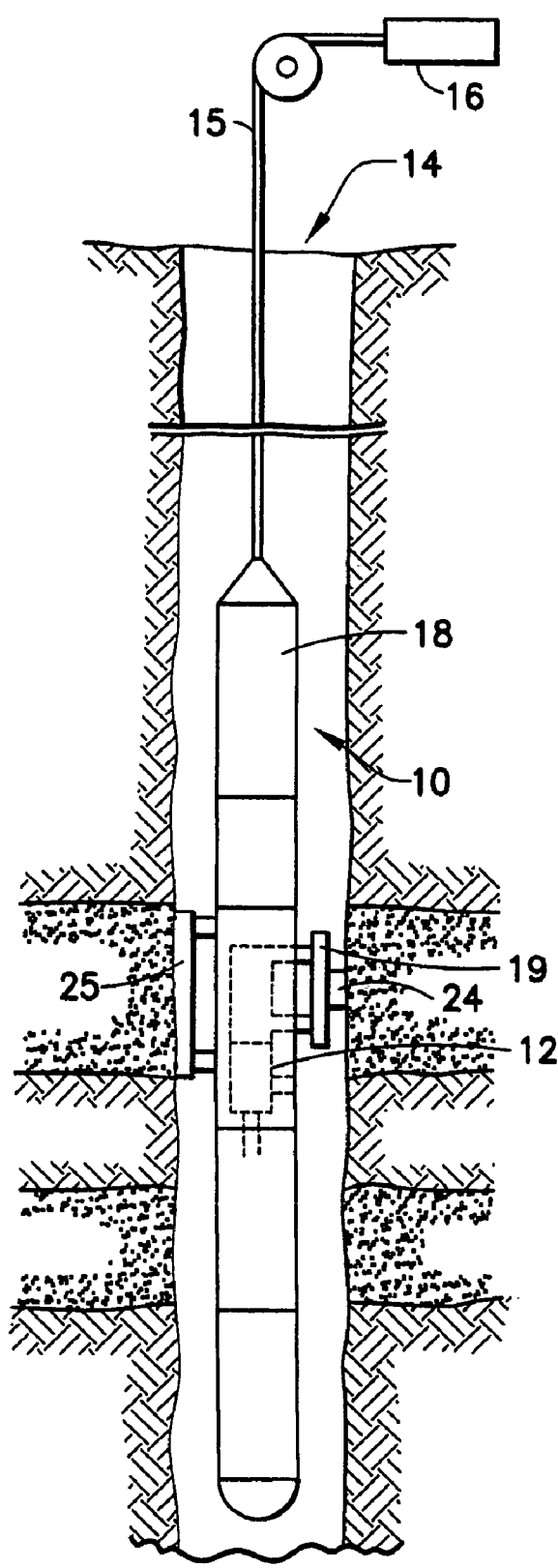
FIG. 1 is a schematic diagram of a wireline tool including a dew precipitation detector according to the invention.

The invention provides a method and apparatus for detecting dew precipitation downhole in real time in retrograde condensates, and for measuring dew precipitation onset pressure. The invention is suitable for use in borehole investigative logging or in production logging. The method includes exciting fluorescence and monitoring fluorescence emitted from a downhole formation fluid sample under conditions of decreasing pressure on the sample. In investigative logging, the ability to detect dew precipitation is important because the presence of dew precipitation renders invalid a fluid sample taken for the purpose of composition analysis. In production logging, it is necessary to know the draw-down pressure at which dew precipitation occurs because this draw-down pressure limits production flow rate.

1) Technical Analysis and Experimental Data

A sample containing retrograde condensates is typically found when a fluid sample is taken from a deep hot oil and gas reservoir by wireline fluid sampling (WFS). Retrograde condensates are susceptible to dew precipitation. Dew precipitation in oilfield fluids is one important form of downhole phase separation, another being bubble creation. Phase separation downhole in oilfield fluids from a particular formation limits the pressure drop that can be used in production of crude oil from that formation, thereby limiting the flow rate of crude oil production from that formation. Phase separation in oilfield fluids is separation into a continuous phase and a discrete phase, either into a gas phase and a liquid phase, or into a continuous liquid phase and a discrete liquid phase. Dew precipitation is of particular concern when attempting to obtain valid samples from deep hot oil and gas reservoirs. For a sample to be valid, it must be of single phase, which means it must be at least free of dew precipitation.

When dew precipitation occurs in a downhole pipe or flow line, dew typically forms first as a mist 21 as shown in FIG. 9A. After dew forms as a mist, most of the dew deposits on the walls of the containing pipe in the form of film 22, as shown in FIG. 9B. Liquid enriched in heavier ends can flow as an annular film on the inner surface of the pipe or flow line, with gas or depleted condensate entrained in the middle of the pipe or flow line. Sometimes mist coalesces into slug form 23 as shown in FIG. 9C.

The phase diagram of FIG. 10 (prior art) shows a pressure reduction (represented by arrow 107 in FIG. 10) taking the fluid from single-phase domain 101 into multi-phase domain 102 to produce dew precipitation as the dew precipitation transition boundary 104 is crossed. (The dew precipitation transition boundary is the single-phase/multi-phase boundary between critical point 105 and cricondentherm 109, as distinct from the bubble creation transition boundary 103 whereon bubbles are created when crossed as by arrow 106). Following entry into the multi-phase domain, mist forms in the sample and optical absorbance increases, and then, as dew accumulates on the window of the optical cell, fluorescence intensity increases.

Figure 11:
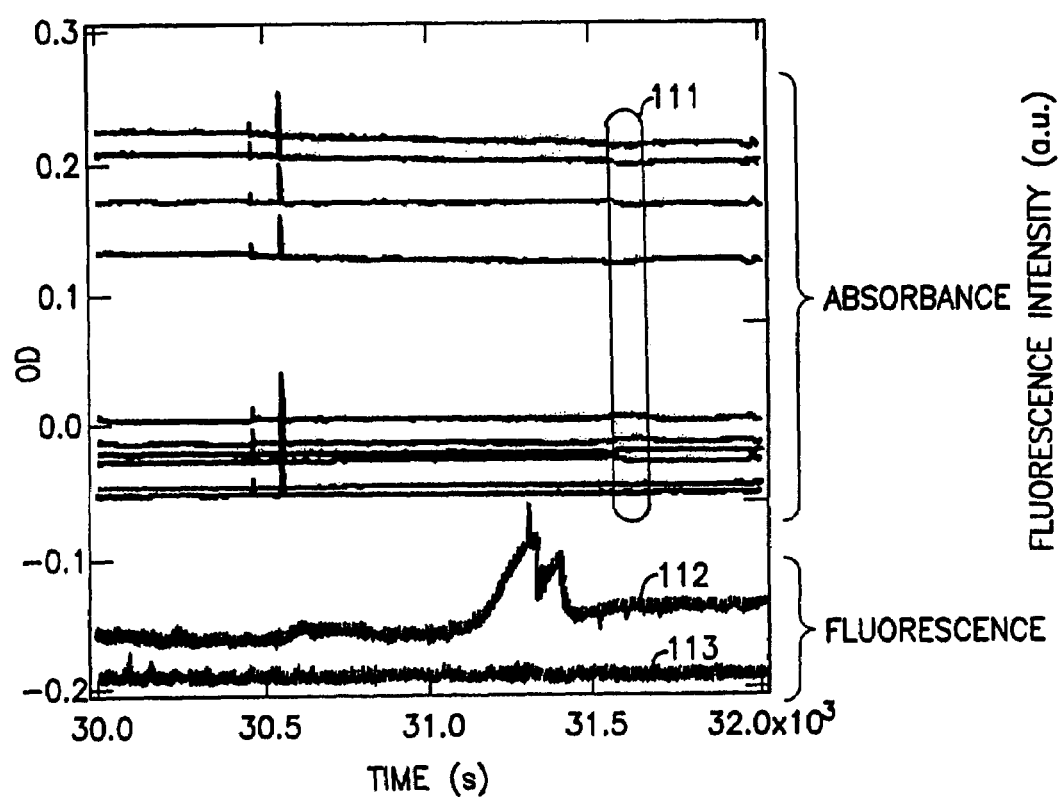
FIGS. 11 and 12 are graphs showing experimental results.
Figure 12:
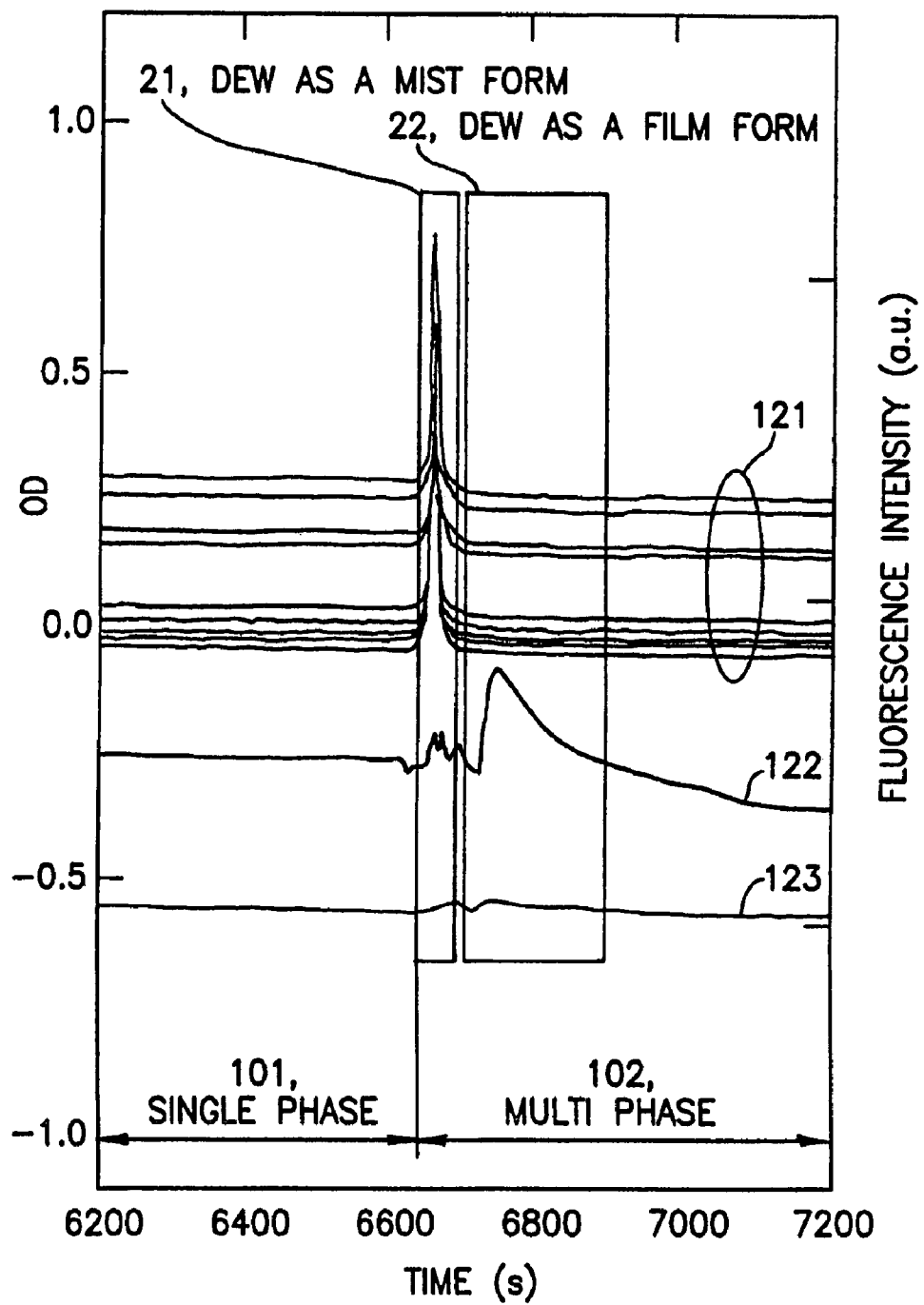

These events are indicated in experimental data plotted in the graphs of FIGS. 11 and 12. FIG. 11 displays ten traces 111 of optical absorbance indicating optical density (OD) and two traces (112 and 113) of fluorescence. Trace 112 is from a first fluorescence channel at 550 nm. Trace 113 is from a second fluorescence channel at 680 nm. The ten upper traces show how OD varies over a period of time following taking a sample. Upper traces 111 show that as pressure is reduced, mist forms in the sample and optical absorbance increases at 30.5 seconds. The two lower traces show how fluorescence varies over the same period of time. The two lower traces show that as dew accumulates on the window of the optical cell, fluorescence intensity increases at approximately 31.3 seconds. Likewise, FIG. 12 shows an increase of absorbance (the spike of traces 121) as the pressure is reduced and mist forms in the sample. FIG. 12 also shows a later increase of fluorescence (traces 122 and 123) as dew forms a film on the window of the optical cell; and that following this there is a decrease of fluorescence, probably due to drainage of the film off the window.

Retrograde condensates are defined by having formation conditions where the formation temperature is between the fluid critical point and the cricondentherm. At the critical point of a fluid ("critical point" is a term used in thermodynamics), distinction between gaseous phase and liquid phase ceases to exist. In most situations, formation fluid has one and only one critical point in the whole pressure and temperature range. The "cricondentherm" is the highest temperature in which dew is still able to precipitate out of mixture, and where the reservoir pressure is above the dew line. FIG. 10 shows critical point 105 and cricondentherm 109. The pressure reduction used for fluid sample extraction can cause dew precipitation. If dew precipitation occurs, it can take the form of a mist, thin film, or relatively large slug, depending on sampling conditions. The phase separation is usually from single-phase to two-phase. (More rarely 3 or 4 phases can occur). In the phase diagram of FIG. 10, a pressure reduction would appear as a descent from the single-phase domain 101 into the multi-phase domain 102. Sampling is an isothermal process, so temperature changes are a secondary issue. Dew precipitation is associated with the discrete phase fluid being enriched in heavier ends, and the continuous phase fluid being depleted. The discrete liquid phase often appears initially as a fog or mist 21 as shown in FIG. 9A. When the discrete fluid phase appears initially as mist, the discrete fluid phase consists of a plurality of droplets separated from one another in a carrier fluid. For dew condensation the higher density hydrocarbon phase typically takes the form of "droplets", and the lower density hydrocarbon phase becomes the continuous phase, sometimes referred to as "gas". This mist can persist depending on downhole conditions such as flow rates and droplet size, and by density contrast between the two phases.

In rare cases three phases can exist. Asphaltenes and wax could precipitate out of fluid as a solid phase in heavy crude, but this is unlikely for a condensate reservoir. More seriously small sand particles could be entrained, but the entrainment of sand particles is not addressed by the present invention. Droplet size depends on the rate and quantity of liquid precipitation. This mist may be detected using conventional optical techniques that measure scattering. The existence of the mist depends on pressure. If the pressure is increased above the dew line, then the mist will disappear, although there may be a time lag.

Depending on conditions, mist droplets can coalesce and adhere to flow line walls resulting in a dramatically reduced surface energy. It is known that, apart from the effects on other potentials such as gravity and electromagnetic charges, liquid phase is most stable when the area of its interface to gas phase is at minimum. So, in the absence of other potentials, a given volume of liquid will tend to coalesce into one large sphere rather than multiple spheres or other forms. The surface energy reduction accompanying coalescence always favors adherence of the mist droplets as a film on the walls of the containing pipe or flow line. With large volumes of liquid precipitation, a slug flow may occur as shown in FIG. 9C. Slug flow of the sort seen with oil sampling can be expected when the pressure drops below the bubble point. Slug flow may be detected using conventional methods that differentiate gas from oil. A GOR gas detection method is disclosed in commonly owned US patent application Ser.

No. 09/686,646 filed Oct. 10, 2000, which is hereby incorporated herein by reference, and which subsequently issued as U.S. Pat. No. 6,476.384 B 1. Another gas detection method is disclosed in commonly owned U.S. Pat. No. 5,167,149 issued Dec. 1, 1992, which is also hereby incorporated herein by reference.

When there is insufficient liquid volume to produce slug flow, enriched condensate flows as an annular film on the inner surface of the flow line with gas or depleted condensate entrained in the middle of the flow line, as shown in FIG. 9B. In this situation, the above-mentioned GOR gas detection method is unlikely to work well because the thickness of the film is much less than the 2 mm path-length of the GOR gas analyzer cell. The above-mentioned GOR gas detection method is also unlikely to work well when the spectrum of the bulk depleted condensate plus liquid film is very similar to the spectrum of the bulk single phase condensate. Furthermore, the GOR gas detector cell is sensitive to index of refraction, and a liquid film enriched in heavier ends has a larger index of refraction than the original condensate. This can be expected to produce erroneous signals.

2) Method of the Invention 2.1) Detecting Dew Precipitation by Measuring a Characteristic of Fluorescence The invention uses a measurement of at least one fluorescence characteristic of a group of fluorescence characteristics, and preferably a measurement of at least one other characteristic, either another fluorescence characteristic of the group of fluorescence characteristics or an optical characteristic of a group of optical characteristics. The group of fluorescence characteristics includes fluorescence intensity, fluorescence spectrum (typically wavelength change or red-shift), and fluorescence lifetime. The group of optical characteristics includes optical absorption. The invention provides a method and apparatus for detecting dew precipitation by detecting dew in any of the three forms: mist form, film form, or slug form. The sample may be a static sample or a flowing sample.

Figure 6:
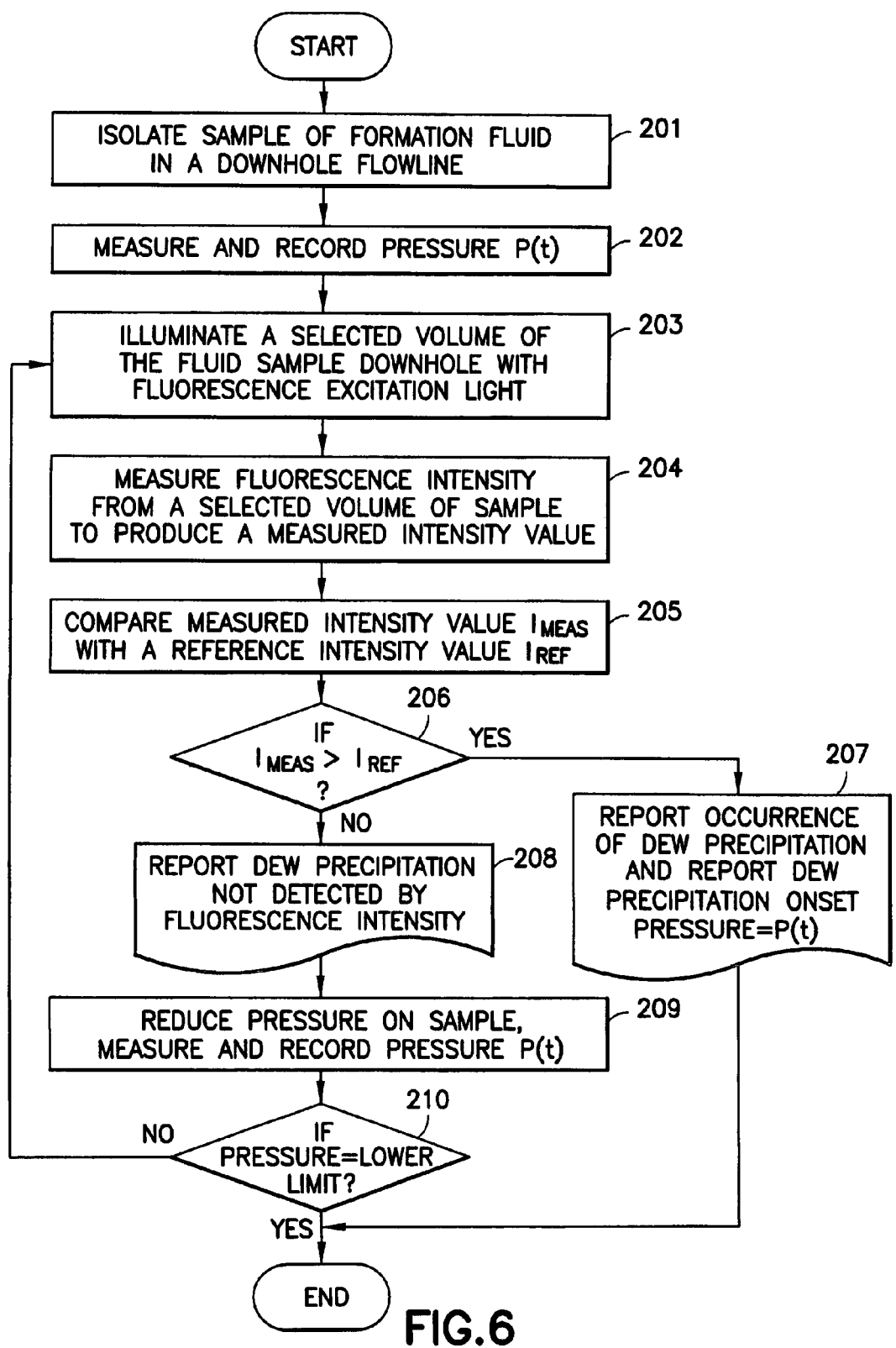
FIG. 6 is a flowchart of a first embodiment of the method of the invention using fluorescence intensity as an indicator of dew in the form of film.

In a first embodiment illustrated in FIG. 6, the invention uses a measurement of fluorescence intensity. In a second (preferred) embodiment illustrated in FIG. 7, the invention uses a measurement of fluorescence intensity and a measurement of fluorescence red-shift. Preferably, the preferred embodiment also uses a measurement of optical absorption. In a third embodiment illustrated in FIG. 8, the invention uses a measurement of fluorescence lifetime.

For colored condensates, the measured fluorescence is optical fluorescence. Optical fluorescence is produced (i.e. excited) by the absorption of visible or UV light. The optical absorption path-length for crude oil is in the order of 0.1–2.0 mm. It is known that the absorption path-length in crude oil decreases exponentially with shorter wavelength excitation so a shorter excitation wavelength produces a shorter path-length. Some embodiments of the invention take advantage of this by providing several light sources of different wavelength that are brought into use dynamically to make best use of the fixed path-length of the optical cell. Because the heavy ends are concentrated in the liquid fraction, the liquid that drops from the condensate will always be darker in color than the single-phase condensate. This darkening of the liquid fraction is accompanied by a higher concentration of fluorophores, an increase in fluorescence intensity (i.e. quantum yield), a red-shift in fluorescence spectrum, and a decrease in fluorescence lifetime. The higher concentration of fluorophores produces red-shift because more energy is transferred. However, too high a concentration of fluorophores may actually result in reduced intensity as the excited aromatics pass energy to larger molecules that generally have smaller quantum yield.

Fluorescence is emitted from a small portion of the sample known as the volume of interrogation. The volume of interrogation is defined by the system optics, and in particular by the intersection of the field of view of the excitation optics and the field of view of detection optics. By proper imaging of the system optics, the volume of interrogation is intentionally small and is located on the fluid sample side of the sample cell window, adjacent to the window.

Liquid film from fluid containing only colorless condensates does not fluoresce under visible light. Embodiments for monitoring fluid containing predominantly colorless condensates use UV excitation. In one embodiment, a real time determination is made to determine whether or not the sample fluid can be excited by visible light. When it is determined that the sample fluid cannot be excited by visible light, UV light is used. Preferably, this switching from visible excitation light to UV excitation light is done downhole on command from surface system 16.

Figure 3:
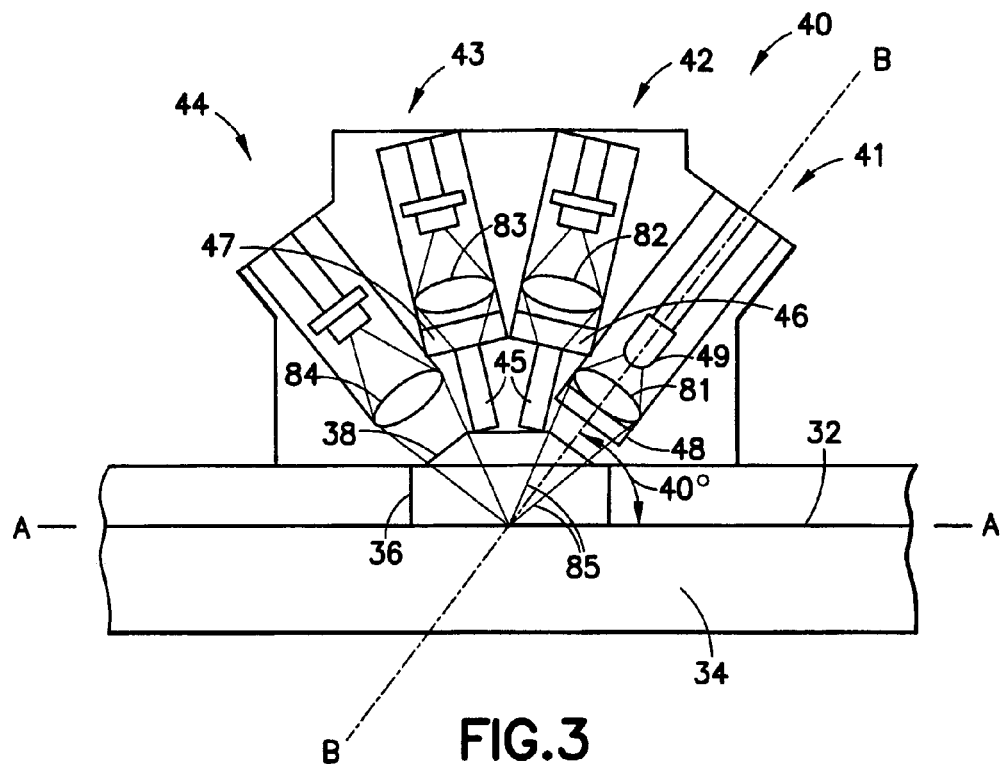
FIG. 3 is a schematic illustration of a first preferred embodiment of a dew precipitation detector according to the invention.
Figure 4:
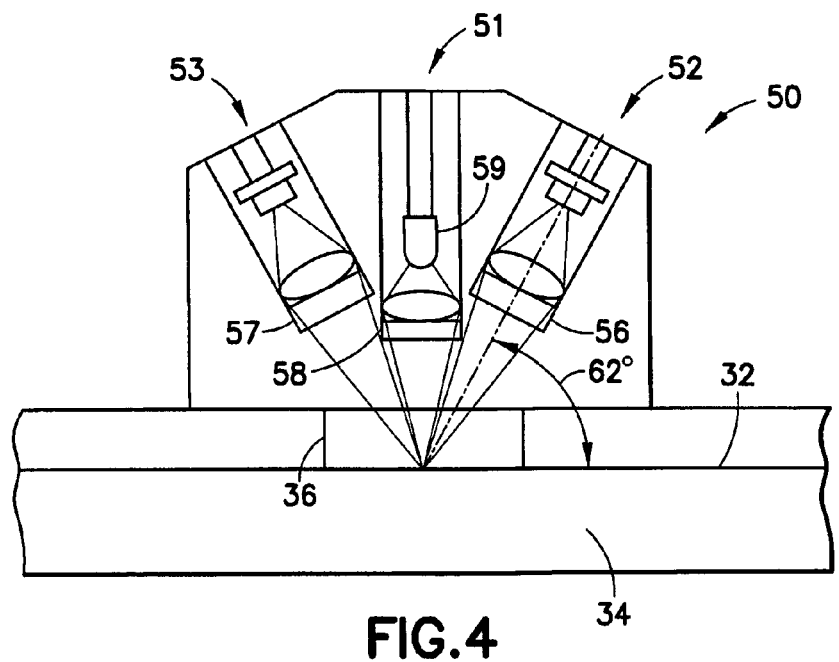
FIG. 4 is a schematic illustration of a second embodiment of a dew precipitation detector according to the invention.

FIGS. 3 and 4 show a single excitation source having a single excitation wavelength, and two detectors detecting at different wavelengths. The invention includes the use of multiple excitation wavelengths to characterize the fluorescence characteristics of the sample fluid. The invention also includes the use of multiple detection wavelengths to characterize the fluorescence characteristics of the sample fluid.

Figure 7:
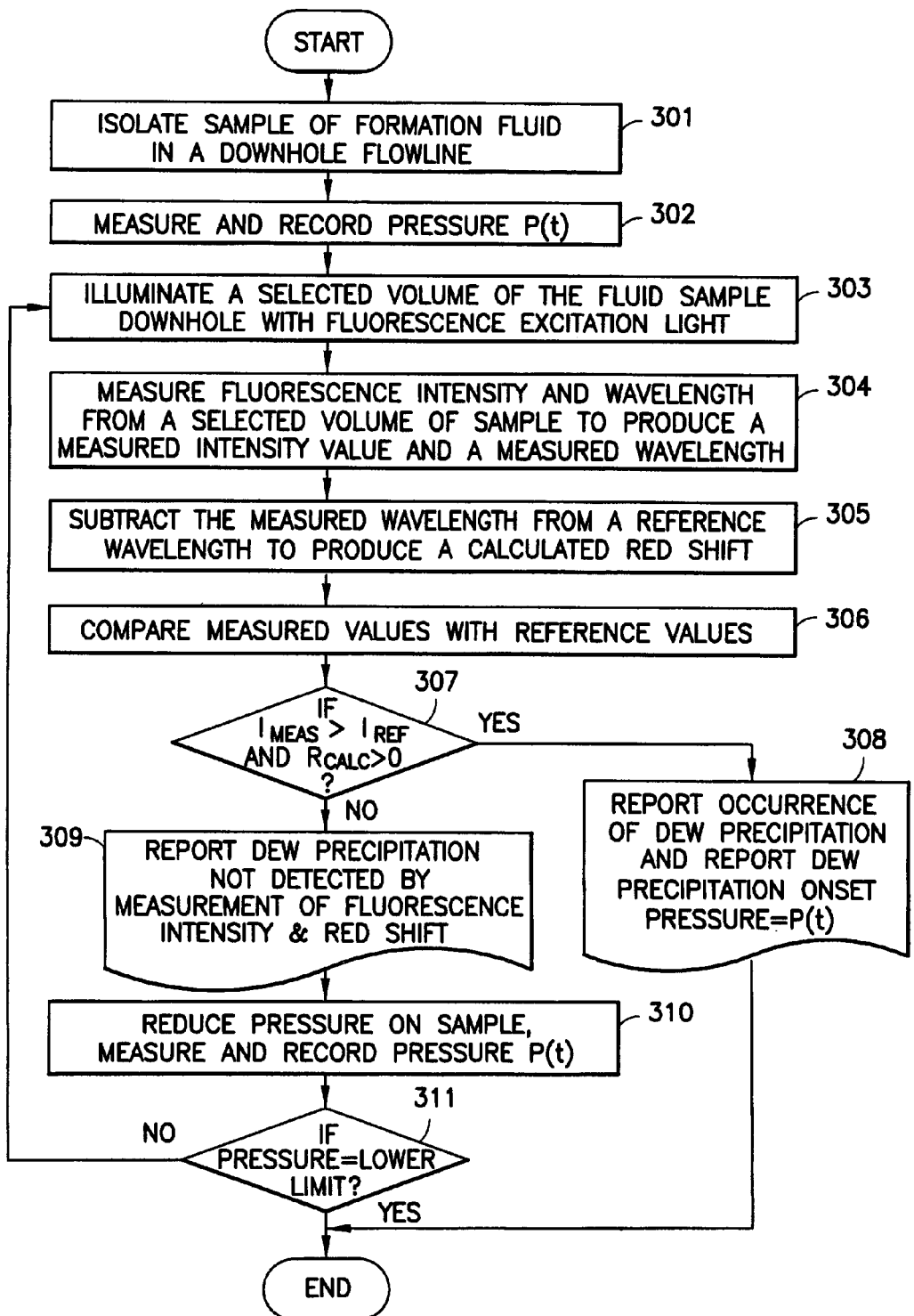
FIG. 7 is a flowchart of a second (preferred) embodiment of the method of the invention using fluorescence intensity and red shift as an indicator of dew in the form of film.

In the second (preferred) embodiment of FIG. 7, two fluorescence characteristics are monitored during drawdown pressure increase. Dew precipitation is indicated by an increase in fluorescence intensity and the presence of red-shift of fluorescence spectrum under condition of reduced pressure, i.e. during a pressure draw-down.

The pressure difference used in taking a sample is preferably optimized to be high enough for the sampling process to be quick, but not so high that the sampling process itself produces dew precipitation.

2.2) Using Measured Fluorescence Intensity Indicative of Absorption of Excitation Wave Condensates that are not strongly colored absorb very little visible excitation light and consequently emit fluorescence at very low levels of intensity. Because a film of dew is enriched in heavier ends, it is darker and more absorptive of visible excitation light, so it produces a higher level of fluorescence intensity. If the optical density for a color channel increases by a factor of 5, a corresponding change in the fluorescence properties is expected. Reduction in light transmission corresponds approximately to increase in fluorescence intensity. As mentioned above, the collection optics is designed to interrogate a small volume of fluid adjacent to the window. Focusing closely on film adjacent to the window has the effect of magnifying the contrast.

2.3) Using Measured Fluorescence Red-Shift

Condensates that are strongly colored absorb visible excitation light to emit fluorescence at high levels of intensity. At high concentrations of fluorophores, a red-shift of the fluorescence spectrum occurs. Under these circumstances, the presence of red-shift alone is indicative of the formation of dew precipitation. Two wavelength channels are use to quantify red-shift. Absolute locations of cutoff wavelength are not critical.

However, red-shift alone is not a good indicator for film formation in light condensate under all circumstances because in heavier crude, blue-shift can be produced by a dispersed asphaltene precipitation. The invention recognizes an increase of fluorescence intensity coupled with a red-shift as indicative of dew precipitation. (An increase of fluorescence intensity coupled with blue-shift is indicative of dispersed asphaltene precipitation).

a. Using Measured Fluorescence Lifetime

Figure 8:
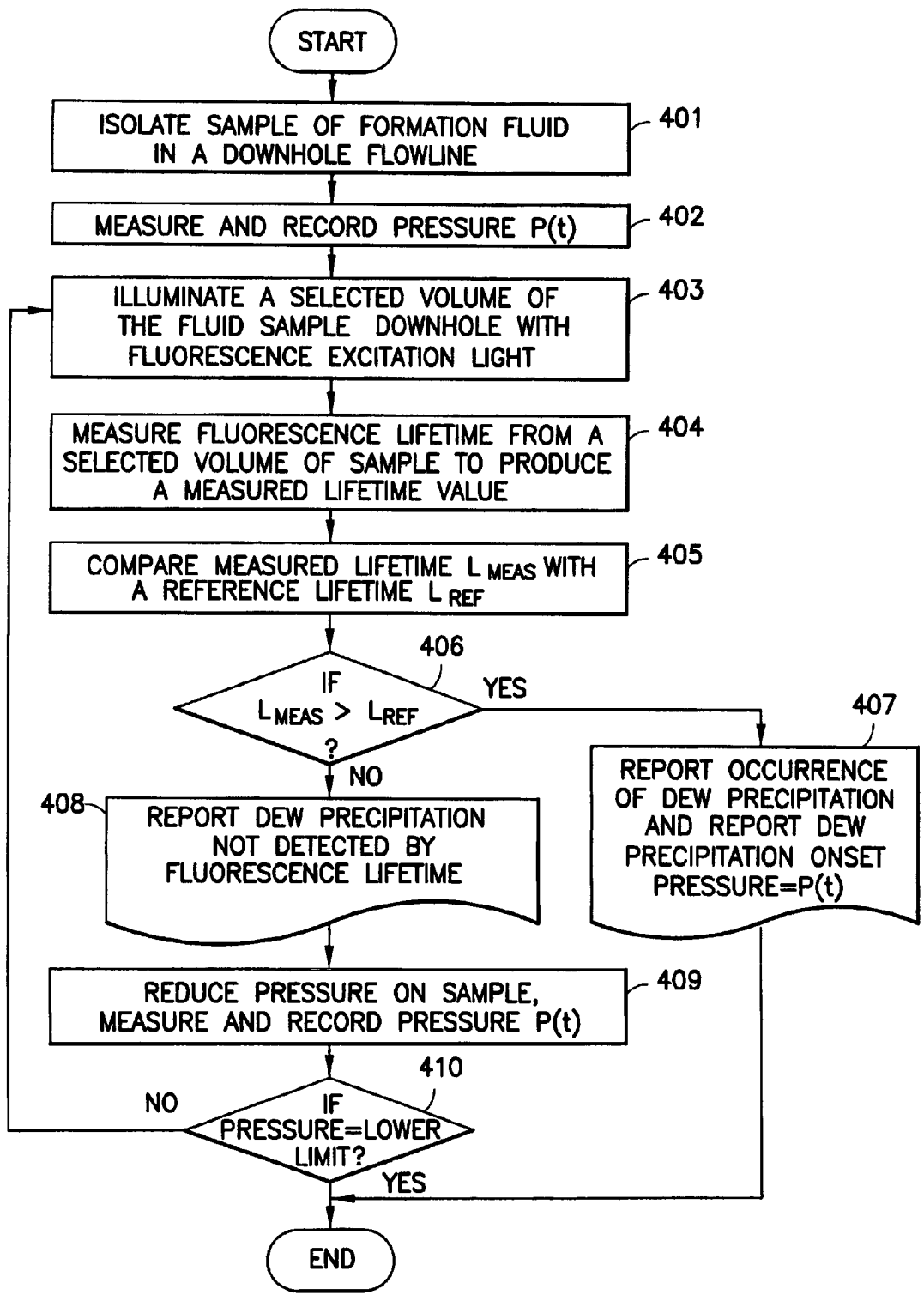
FIG. 8 is a flowchart of a third embodiment of the method of the invention using fluorescence lifetime as an indicator of dew in the form of film.

In the third embodiment of FIG. 8, the invention uses a measurement of fluorescence lifetime. Fluorescence lifetime generally decrease with the formation of a film. Fluorescence lifetime is more difficult to measure than intensity and spectral shift but it offers high sensitivity because the change in lifetime can be dramatic. Lifetime can change from about 100 nanoseconds down to approximately 10 nanoseconds.

a. Using Measured Light Transmission in the Mist Phase

The preferred embodiment, in combination with fluorescence measurements, preferably also uses measured light transmission to detect dew precipitation in the mist phase. Mist form dew increases light scattering and thereby reduces light transmission. So dew precipitation is detected by measuring reduced light transmission at a predetermined time after taking a sample.

a. Using Measured Optical Reflectance Indicative of Slug Flow

In the preferred embodiment, the tool preferably includes the ability to detect the slug form of dew as a change in reflectance.

a. Combinations of Measured Characteristics

The several methods discussed above are effective for dew detection in the three different forms of dew as shown in Table 1 below.

TABLE 1

|  | Mist (Fog) | Film (Annular Flow) | Slug (Large Bulk) |
| --- | --- | --- | --- |
| Fluorescence Intensity | No | Yes | Yes* |
| Fluorescence Red Shift | — | Yes | Yes* |
| Fluorescence Lifetime | — | Yes | Yes* |
| Optical Absorption | Yes | No | Yes* |

*Measuring over a sufficiently long period of time

3) Apparatus 3.1) Preferred Embodiments

FIG. 1 is a schematic diagram of a wireline tool 10 including a dew precipitation detector 12 according to the invention. Tool 10 is suspended in borehole 14 from the lower end of a logging cable 15 that is connected in a conventional fashion to a surface system 16 incorporating appropriate electronics and processing systems for control of the tool. Tool 10 includes an elongated body 18 that carries a selectively extendible fluid admitting assembly 19. Such fluid admitting assemblies are described in U.S. Pat. No. 4,860,581, hereby incorporated herein by reference. Elongated body 18 also carries selectively extendible anchoring members 24, 25 that are arranged on opposite sides of the body. Fluid admitting assembly 19 is equipped for selectively sealing off or isolating portions of the wall of the borehole such that pressure or fluid communication with the adjacent earth formation is established. Dew precipitation detector 12 is also included within the tool body, through which the contained fluid flows. The fluid can than be expelled through a port (not shown) back into the borehole, or can be sent to one or more sample chambers for recovery at the surface.

Figure 2:
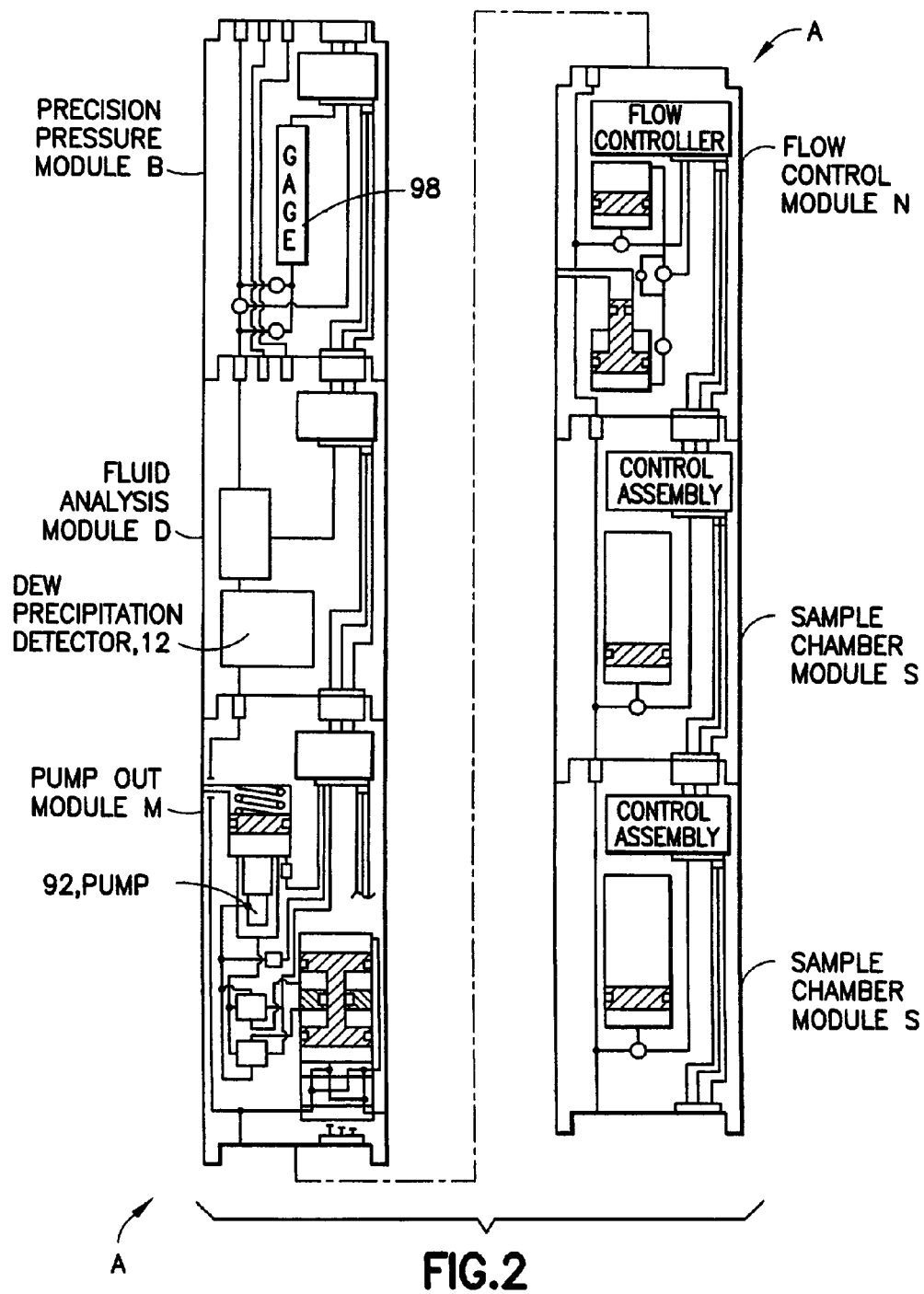
FIG. 2 is a schematic diagram locating the dew precipitation detector in the fluid analysis module of the wireline tool of FIG. 1.

FIG. 2 locates dew precipitation detector 12 in fluid analysis module D of wireline tool 10. FIG. 2 shows pressure gage 98 in precision pressure module B upstream of detector 12. Pressure gage 98 performs the measurements of pressure in the methods of the invention. FIG. 2 also shows pump 92 in Pump out module M, and flow control module N, both downstream of detector 12. Pump 92 provides the pressure to drive fluid sample through the flow line and the sample cell and to produce the pressure reduction for the method of the invention. Tool 10 also includes sample chambers S for capturing and carrying fluid samples to the surface for analysis. A description of a wireline tool such as shown in FIG. 2, but without the dew precipitation detector of the present invention, is found in U.S. Pat. No. 4,860,581, issued Aug. 29, 1989, to Zimmerman et al. A copy of U.S. Pat. No. 4,860,581 is hereby incorporated herein by reference.

FIG. 3 shows detail of preferred optics 40 of dew precipitation detector 12. Detector 12 is capable of detecting phase separation using one or more of the methods described above. Preferred optics 40 includes a portion of flow line 32 defining fluid sample cell 34, a sapphire optical window 36, a sapphire optical prism 38, excitation light source (470 nm) 41 with light-emitting diode (LED) 49 and converging lens 81 focusing light rays 85, first fluorescence detector (550 nm) 42 with converging lens 82, second fluorescence detector (680 nm) 43 with converging lens 83, light reflection detector (470 nm) 44 with converging lens 84, two glass conduits 45, short-pass optical filter (500 nm) 48, long-pass optical filter (550 nm) 46, and long-pass optical filter (680 nm) 47. The tilt of excitation light source axis B—B away from the fluid interface of sapphire optical window 36 (line A—A) is preferably set, for sapphire, to about 40°. Detector 12 also includes data base means (not shown), and a processing means (not shown).

Fluids drawn from the formation into fluid sample cell 34 are illuminated by excitation light. Emitted fluorescent light is detected to produce fluorescence intensity and other signals. The signals are processed, based on information in the data base relating to the different types of light, to detect dew precipitation and to trigger storage of dew precipitation onset pressure. The excitation wavelength is preferably 470 nm. The fluorescence detection wavelengths are preferably 550 nm and 680 nm. Pressure on the sample is provided by a piston-type pump 92. The fluid sample cell, with its associated optics system and isolation valves, is capable performing optical analysis on a static sample or a flowing sample.

Dew precipitation detector 12 measures fluorescence intensity, and preferably also fluorescence red-shift, in real time in the bore hole.

FIG. 4 shows first alternative optics 50. Optics 50 includes the same type of fluid sample cell 34, and the same type of optical window 36 as the preferred embodiment of FIG. 2. However, optics 50 includes excitation light source (470 nm) 51 with light-emitting diode (LED) 59, first fluorescence detector (550 nm) 52, second fluorescence detector (680 nm) 53, short-pass optical filter (500 nm) 58, long-pass optical filter (550 nm) 56, and long-pass optical filter (680 nm) 57 in a different physical arrangement.

Figure 5:
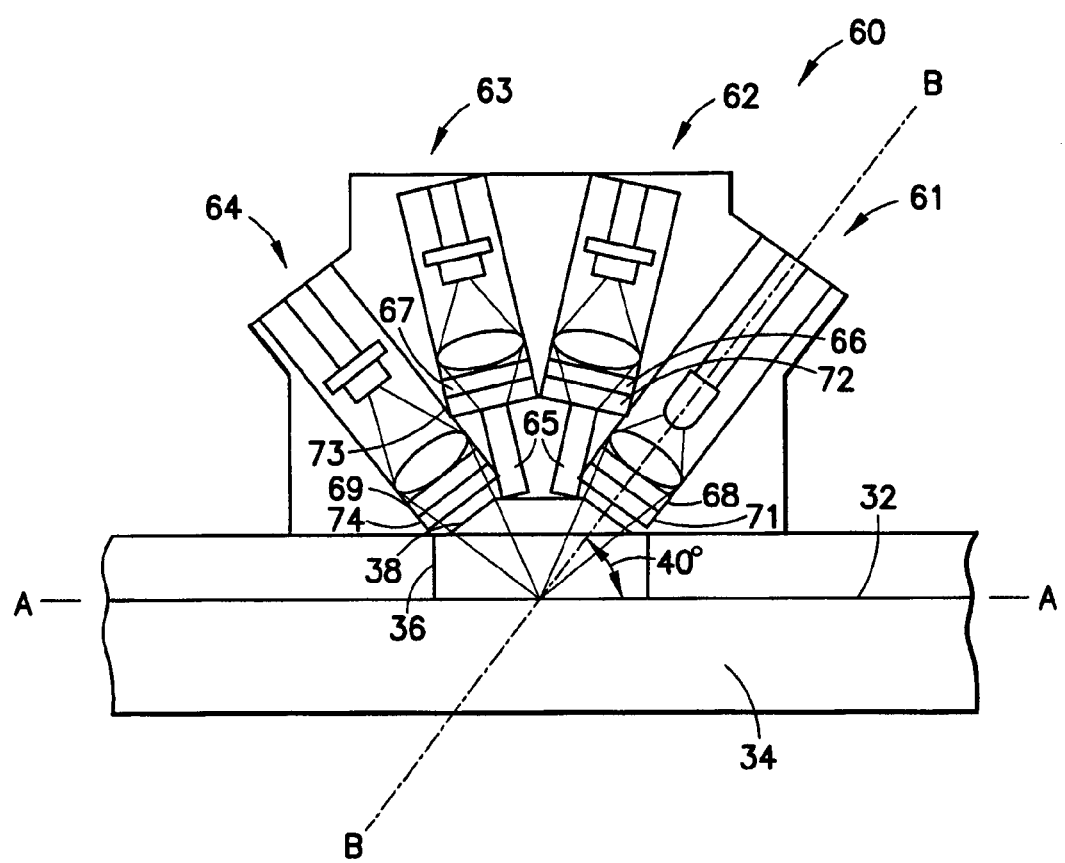
FIG. 5 is a schematic illustration of a third embodiment of a dew precipitation detector according to the invention.

FIG. 5 shows the use of polarizers in a similar optics arrangement to that of the first preferred embodiment. The use of polarizers is preferred in some situations, depending on the colorization of the formation fluid. Generally, the use of polarizers is preferred when the formation fluid is sufficiently colorized. Polarizers are inserted in cross configuration so that only fluorescence signal can reach photodetectors. The use of polarizers can improve signal to noise-ratio in the fluorescence intensity measurement. The excitation light is p-polarized (in-plane). By using p-polarization on excitation light, the reflection coefficient is reduced at the sapphire/fluid interface. In addition, the use of s-polarization on the fluorescence detection channels, blocks source light reflected by specular reflection. The use of polarization filters coupled with wavelength solution filters reduces optical noise significantly. When properly configured and properly applied, the benefit of reduced optical noise outweighs the reduction of signal power level resulting from the use of polarizing filters.

Like preferred optics 40, optics 60 includes a portion of flow line 32 defining fluid sample cell 34, a sapphire optical window 36, and a sapphire optical prism 38. In substantially the same configuration as preferred optics 40, optics 60 includes excitation light source (470 nm) 61, first fluorescence detector (550 nm) 62, second fluorescence detector (680 nm) 63, fluorescence reflection detector (470 nm) 64, two glass conduits 65, long-pass optical filter (550 nm) 66, and long-pass optical filter (680 nm) 67. Unlike preferred optics 40, optics 60 includes short-pass optical filter (500 nm) 68 in excitation light source (470 nm) 61, and short-pass filter (500 nm) 69 in fluorescence reflection detector (470 nm) 64. Unlike preferred optics 40, optics 60 also includes polarizing filters.

Polarizing filters are used in optics 60 as follows. Referring to FIG. 4, p-polarized polarizing filter 71 is provided in the light path of excitation light source (470 nm) 61. N-polarized polarizing filters 72 and 73 are provided in the light path of first and second fluorescence detectors 62 and 63, respectively. P-polarized polarizing filter 74 is provided in the light path of fluorescence reflection detector (470 nm) 64.

a. Maximizing Fluorescence Signal—Maximizing Excitation Power

In the embodiments of FIGS. 2–5, a shorter wavelength light may be used for both excitation and detection. Using shorter wavelength light excites aromatics with higher quantum yield and results in stronger fluorescence. Tentatively, the excitation wavelength was set to be 470 nm and fluorescence detection was set to be 550 nm and 680 nm, but simply providing a shorter wavelength light source and providing optical filters having a correspondingly shorter pass-band easily shortens the operational wavelength.

a. Minimizing Optical Noise—Optical Filtering by Optics Design

In the preferred embodiments of FIG. 3, optical noise is minimized by directing specular reflection of excitation light away for the collection optics of the fluorescence detectors.

a. Minimizing Optical Noise—Optical Filtering of Reflected Light

In the embodiments of FIGS. 3–4, band-pass filters or long-pass filters are provided to prevent scattered excitation light from reaching the detectors.

a. Minimizing Optical Noise—P-Polarized Filtering of Excitation Light and Brewster's Angle In the embodiment of FIG. 5, the amount of reflected light entering the interrogation volume is further reduced by p-polarizing excitation light and directing the p-polarized light onto the window at Brewster's angle. This minimizes optical noise at the sapphire/sample fluid interface. At Brewster's angle the p-polarized excitation light will be 100% transmitted but reflected light will be blocked. To accomplish this, as shown in FIG. 5, the tilt of excitation light source axis B—B away from the fluid interface of sapphire optical window 36 (line A—A) is set to Brewster's angle which, for sapphire, is about 40°. Reflection loss of excitation light become significant when the incident angle exceeds Brewster's angle, and all excitation light is reflected if the angle exceeds the critical angle.

Brewster angle $\theta_B$ is given in equation (1), $$\theta_B = \arctan(n_2/n_1) \quad (1)$$

wherein $n_1$ denotes the refractive index of the window material and $n_2$ denotes the refractive index of the fluid. The Brewster angle is calculated to be 38.3° for a fluid refractive index of 1.4 for a sapphire window ($n_1$=1.77). For a diamond window ($n_1$=2.42) the Brewster angle is calculated to be 30.0°.

3.6) Minimizing Optical Noise—S-Polarized Filtering of Light Received at Detectors In the embodiment shown in FIG. 5, excitation light is p-polarized and light recieved on the fluorescence detection channels is s-polarization filtered. This reduces optical noise because specular reflections of excitation light are largely blocked.

What is claimed is:

1. A method for detecting dew precipitation in a sample of formation fluid located downhole in an oilfield reservoir, comprising:
    (a) isolating a sample of formation fluid downhole;
    (b) illuminating the sample downhole with fluorescence excitation light;
    (c) measuring at least one characteristic of fluorescence emission from the sample;
    (d) reducing pressure on the sample;
    (e) repeating steps (b) to (d); and
    (f) detecting dew precipitation when a change is detected in a parameter that is a function of the at least one characteristic of fluorescence emission.

2. A method according to claim 1, further comprising:
    (g) setting dew precipitation onset pressure equal to pressure on the sample when the change in the parameter is detected.

3. A method according to claim 1, wherein the parameter includes a function of fluorescence intensity, and the change includes an increase in fluorescence intensity.

4. A method according to claim 3, wherein the parameter also includes a function of at least one other fluorescence characteristic.

5. A method according to claim 4, wherein the at least one other fluorescence characteristic is fluorescence red shift.

6. A method according to claim 5, wherein the parameter is a function of fluorescence intensity and fluorescence red shift, and the change is an increase in fluorescence intensity and detection of fluorescence red shift.

7. A method according to claim 6, wherein the function includes a ratio of a measured intensity at a first wavelength to a reference intensity.

8. A method according to claim 7, wherein the reference intensity is a function of a measured intensity at a second wavelength.

9. A method according to claim 1, wherein the parameter is a function of fluorescence lifetime, and the change is decrease in fluorescence lifetime.

10. A method according to claim 1,
    wherein isolating a fluid sample downhole includes enclosing the sample in a fluid sample cell having a window;
    wherein illuminating the fluid sample includes selectively illuminating the fluid sample in an interrogation volume adjacent to the window, and wherein measuring at least one characteristic of fluorescence emission includes measuring fluorescence intensity emitted from the interrogation volume.

11. A method according to claim 10, wherein the fluorescence excitation light is polarized and directed onto the window at the Brewster angle.

12. A method according to claim 10, wherein the fluorescence excitation light is polarized in a first direction, and fluorescence light received by a detector is polarized in a second direction, the second direction being orthogonal to the first direction.

13. A method for detecting dew precipitation in a sample of formation fluid located downhole in an oilfield reservoir, comprising:
  (a) illuminating the fluid sample downhole with fluorescence excitation light at a first excitation wavelength;
  (b) measuring fluorescence intensity emitted from the fluid sample under reduced pressure in a fluid sample cell to produce a measured intensity value; and
  (c) detecting dew precipitation when the measured intensity value is greater than a reference intensity value.

14. A tool for detecting dew precipitation in a fluid sample located downhole in an oilfield reservoir, comprising:
  a tool body including a fluid sample cell adapted to take a sample of formation fluid downhole in the oilfield reservoir;
  means for isolating a sample of formation fluid downhole;
  means for illuminating the sample downhole with fluorescence excitation light;
  means for repeatedly reducing pressure on the sample and measuring at least one characteristic of fluorescence emission from the sample; and
  means for detecting dew precipitation when a change is detected in a parameter that is a function of the at least one characteristic of fluorescence emission.

15. A tool for detecting dew precipitation in a fluid sample located downhole in an oilfield reservoir, comprising:
  a tool body including a fluid sample cell adapted to take a sample of formation fluid downhole in the oilfield reservoir;
  means for illuminating the fluid sample downhole with fluorescence excitation light at a first excitation wavelength;
  means for measuring fluorescence intensity emitted from the fluid sample under reduced pressure in a fluid sample cell to produce a measured intensity value; and
  means for detecting dew precipitation when the measured intensity value is greater than a reference intensity value.

* * * * *